United States Patent [19]

Aboczky

[11] Patent Number: 4,994,064
[45] Date of Patent: Feb. 19, 1991

[54] INSTRUMENT FOR ORIENTING, INSERTING AND IMPACTING AN ACETABULAR CUP PROSTHESIS

[76] Inventor: Robert I. Aboczky, 323 E. Saddle River Rd., Upper Saddle River, N.J. 07458

[21] Appl. No.: 454,432

[22] Filed: Dec. 21, 1989

[51] Int. Cl.⁵ .............................................. A61F 5/04
[52] U.S. Cl. ...................................................... 606/91
[58] Field of Search ..................... 606/91, 90, 86, 99, 606/100; 623/16, 18, 22

[56] References Cited

U.S. PATENT DOCUMENTS

| | | | |
|---|---|---|---|
| 3,859,992 | 1/1975 | Amstutz | 606/91 |
| 4,305,394 | 12/1981 | Bertuch, Jr. | 606/91 |
| 4,475,549 | 10/1984 | Oh | 606/91 |
| 4,662,891 | 5/1987 | Noiles | 606/91 |
| 4,716,894 | 1/1988 | Lazzeri et al. | 606/91 |

Primary Examiner—David J. Isabella
Attorney, Agent, or Firm—Anthony F. Cuoco

[57] ABSTRACT

An instrument for implanting an acetabular cup prosthesis in a patient's acetabulum. The cup is gripped on the base of the instrument and is aligned and inserted in accordance with a plane normal to the plane in which a patient is positioned and normal to a line between the right and left anterior/superior iliac spines. With the acetabular cup so aligned, the cup is impacted to be retained in a prepared acetabulum. The instrument is actuated for gripping the cup for the aforenoted alignment, insertion and impaction and is thereafter actuated for releasing the cup so that the instrument can be removed from the cup without disturbing the position thereof.

12 Claims, 2 Drawing Sheets

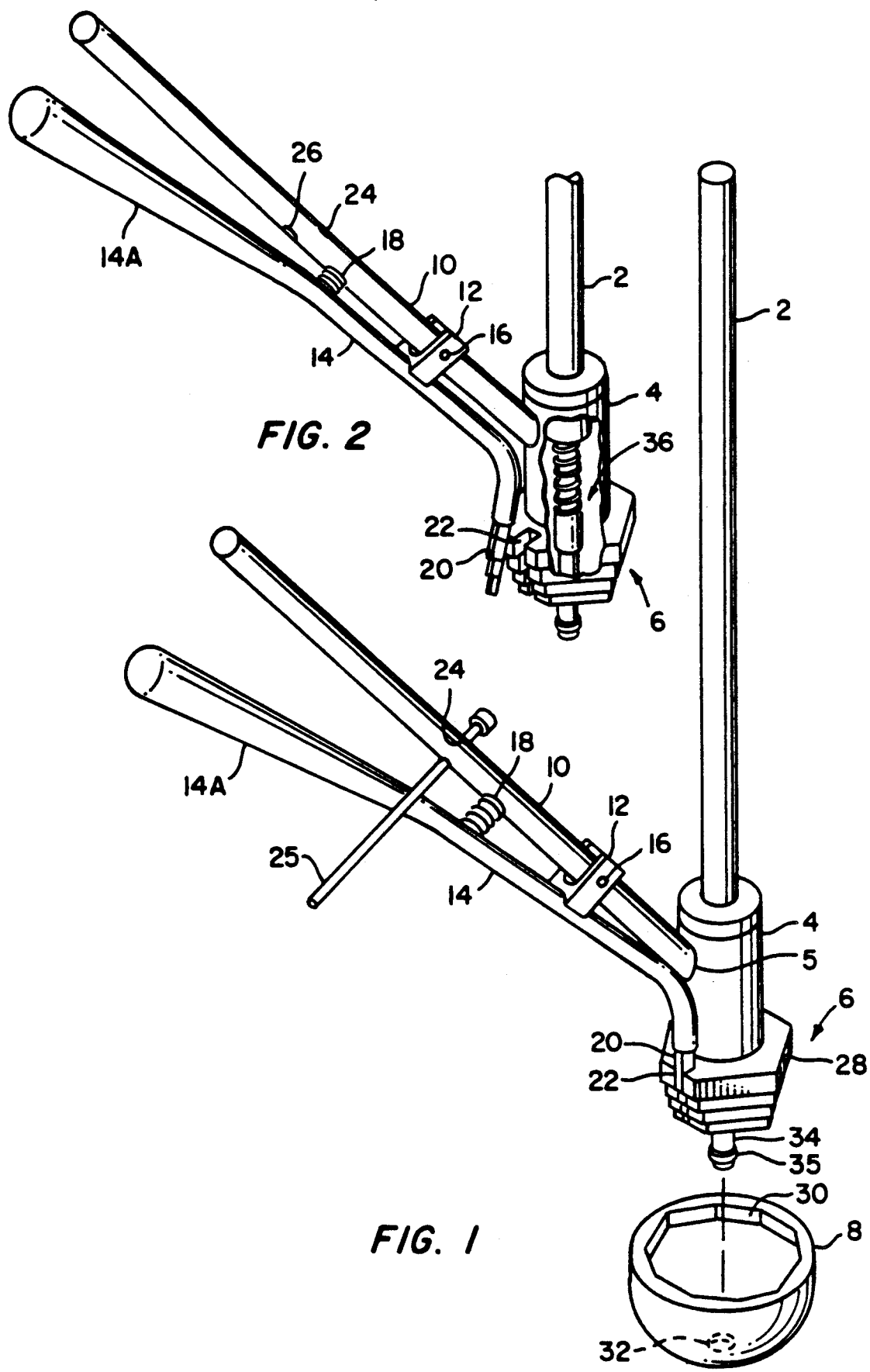

INSTRUMENT FOR ORIENTING, INSERTING AND IMPACTING AN ACETABULAR CUP PROSTHESIS

BACKGROUND OF THE INVENTION

A total hip replacement procedure has been developed by Howmedica Division of Pfizer Hospital Products, Inc., Rutherford, N.J., and is described in a monograph entitled *The P.C.A. Primary Hip System Surgical Technique* prepared and published by Pfizer Hospital Products, Inc. in 1988. Howmedica and P.C.A. are registered trademarks of Pfizer Hospital Products, Inc.

The described surgical technique includes implanting an acetabular outer shell or cup prosthesis after appropriately preparing the acetabulum for the implantation. The actual implantation includes orienting, inserting and impacting the acetabular cup in the acetabulum.

Prior to the present invention, a variety of separate instruments have been required to accomplish the implantation. This has been found to be disadvantageous, particularly in view of the time and inconvenience required in switching from one instrument to another, which prolongs the overall operative time. In this connection it will be noted that a major problem encountered in performing surgical procedures such as herein referred to is the risk of infection of the operative area. This risk increases as the operative time increases, and hence it is most desirable to shorten the operative time to the greatest extent possible. Moreover, due to the nature of the procedure, it is imperative that it be performed under circumstances most auspicious to the patient and to the surgeon.

The present invention overcomes the aforenoted disadvantages and simplifies the implantation, in that only one instrument is required for all of the segments of the procedure. With the instrument to be herein described, an estimated fifteen to twenty minutes of operative time is saved, which is desirable for the reasons aforenoted.

Accordingly, it is the object of the present invention to provide a single instrument for orienting, inserting and impacting an acetabular cup in a prepared acetabulum as part of a total hip replacement procedure, whereby said procedure is simplified, made more convenient and is performed in a time less than would otherwise be the case.

SUMMARY OF THE INVENTION

This invention contemplates an instrument for orienting, inserting and impacting an acetabular cup prosthesis as part of a total hip replacement procedure. The instrument includes an impact rod having a base with a shaped end. A coupling rod is affixed to the base of the impact rod and extends angularly therefrom. The coupling rod supports a spring biased pivoting rod having a shaped end which is pivotable away from and toward the shaped end of the impact rod. The shaped end of the impact rod has a slot and the pivoting rod is normally spring biased so that the end thereof is received in the slot, whereby the shaped ends of the impact and pivoting rods cooperatively mate for supporting the acetabular cup. When the pivoting rod is pivoted away from the impact rod, the spring compresses and the shaped end of the pivoting rod is displaced out of the slot to grip the cup in a retaining relationship, whereby the cup is oriented and inserted in the acetabulum. The supporting rod carries a pair of holes angularly displaced relative to each other and one of said holes, depending on whether the procedure is being performed on the right or left side of the patient, carries an alignment bar.

In using the instrument, the coupling rod is disposed normal to the plane in which a patient is supported, which is a substantially horizontal plane. The alignment bar is aligned normal to a line which crosses from the patient's posterior superior iliac spine to the anterior superior iliac spine, whereby the cup, gripped as aforenoted, is oriented for insertion into the acetabulum.

Upon the cup being so oriented and inserted, the impact rod is impacted, whereby the cup is seated in the acetabulum either by way of a press fit or by cementing. Upon the cup being seated, the pivoting rod is pivoted against the bias of the spring, whereby the shaped end of the pivoting rod is disposed in the slot in the shaped end of the impact rod. The retaining grip on the cup is thereby released, whereby the instrument is removed from the cup without disturbing its seating.

BRIEF DESCRIPTION OF THE DRAWINGS

FIG. 1 is an exploded perspective representation showing the instrument of the invention and an acetabular cup which is retained thereby for being oriented, inserted and impacted into the acetabulum of a patient.

FIG. 2 is a partially cut away perspective representation showing a particular feature of the invention wherein the base and end of the impact rod are adapted via a biasing spring arrangement for receiving acetabular cups.

DETAILED DESCRIPTION OF THE INVENTION

Figure 3:
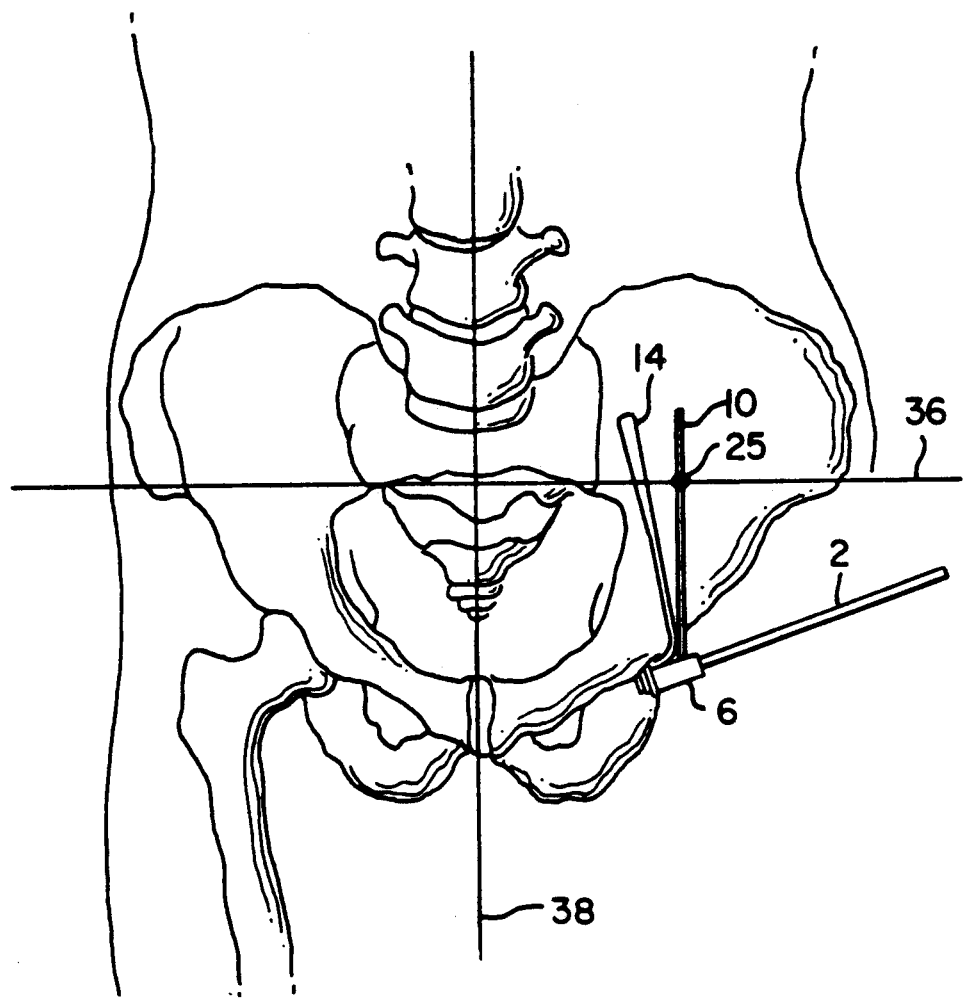
FIG. 3 is a diagrammatic representation showing a line between the right and left anterior/superior iliac spines, and which line is used for aligning the instrument of the invention.

With reference to FIGS. 1 and 2, an impact rod is designated by the numeral 2. Impact rod 2 has a base 4 integral therewith and base 4 has an end 6 integral therewith and shaped in a plurality of step-like gradations 28 for supporting an acetabular cup 8 in a manner which will be hereinafter described.

A coupling rod 10 is affixed to base 4 of impact rod 2 as by welding or the like at 5 and extends angularly therefrom. A clevis-like member 12 is formed integral with a pivoting rod 14. Pivoting rod 14 extends first at a relatively small angle from coupling rod 10 and then at a larger angle to form a handle or gripping portion 14A of rod 14. Coupling rod 10 is supported in the open portion of clevis-like member 12 and is secured therein via a pin 16.

A spring 18 is disposed so as to be captured between coupling rod 10 and pivoting rod 14 above clevis 12. Pivoting rod 14 is normally biased by spring 18 so that a shaped end 20 thereof extends substantially parallel to impact rod 2 and is disposed in a slot 22 in shaped end 6 of impact rod 2. When rod 14 is pivoted about pin 16 toward rod 2 as by squeezing rod 10 and rod 14 at handle portion 14A, spring 18 is compressed and end 22 of rod 14 is displaced from slot 20 as shown in FIG. 2. Thus, when end 20 of pivoting rod 14 is disposed in slot 22, end 6 is adapted for supporting acetabular cup 8 on an appropriate continuous step-like gradation. When end 20 is displaced out of the slot the cup is gripped by end 20 for retaining the cup so supported.

It will be understood that rods 2, 10 and 14 are in the same plane. With particular reference to FIG. 2, rod 10 carries a through hole 24 and another through hole 26, said holes being longitudinally displaced from each other above spring 18. The axis of one of the holes 24 and 26 is displaced by approximately thirty-five degrees in one direction from the common plane of rods 2, 10 and 14 and the axis of the other of the holes 24 and 26 is displaced approximately thirty-five degrees in another direction from the common plane of the rods. As illustrated in FIG. 1, one of the holes 24 and 26 (hole 24 being illustrated for purposes of example), depending on whether the procedure is being applied to the patient's right or left side, carries a removable alignment pin 25 having a purpose which will be hereinafter described.

With continued reference to FIGS. 1 and 2, it will be seen that end 6 of impact rod 2 is formed in step-like gradations 28 as aforenoted, with four such gradations being shown for purposes of illustration. The smallest gradation is at the bottom of end 6 and the largest gradation is at the top thereof. Each of the gradations 28 is shaped in a polygonal configuration, with a hexagon being shown for purposes of illustration.

Each of the step-like gradations 28 is adapted for supporting an acetabular cup 8 of a different size, i.e. diameter and depth. Thus, the smallest acetabular cup 8 fits on the lowermost gradation 28 and the largest acetabular cup fits on the uppermost gradation 28. In this regard, it will be recognized that acetabular cups 8 are substantially semi-spherical in shape and have an internal polygonal mounting rim 30 extending circumferentially therearound. For purposes of illustration, surface 30 is shown shaped as a decagon.

Thus, as will be discerned from FIG. 1, an acetabular cup 8 of a desired size is disposed over end 6, with the appropriate gradation 28 at least partly engaging internal rim 30 of cup 8. With the polygonal configuration of gradations 28 and rim 30 being different as described, the painstaking and time consuming alignment of each of the gradation sides with each of the rim sides is avoided as would not be the case if both polygonal configurations were the same.

Cup 8 is fabricated with a centrally disposed through hole 32 on the bottom thereof as will be recognized by those skilled in the art. A pin 34 extends from the lowermost gradation 28 and into hole 32. Pin 34 has a shoulder 35 and is spring biased via a spring arrangement 36 as shown in FIG. 2, whereby the pin is displaceable into and out of end 6 and base 4 as will be discerned from the Figure. The purpose of pin shoulder 35 is to limit the extension of pin 34 into hole 32 to prevent the pin from extending through the hole into the acetabulum. The pin is displaceable against the bias of spring arrangement 36 so that end 6 can receive the largest acetabular cup 8 on the uppermost polygonal gradation 28.

With an acetabular cup 8 so disposed on end 6, rod 10 and rod 14 at handle portion 14A are grasped and squeezed to pivot rod 14 against the bias of spring 18, whereupon end 20 of rod 14 is displaced out of slot 22 of end 6 to positively grip and retain the cup as will now be understood.

USE OF THE INVENTION

In using the instrument described and with an acetabular cup 8 gripped and retained as aforenoted, coupling rod 10 is disposed perpendicular to the plane in which the patient is supported, which is a substantially horizontal plane. Alignment bar 25 extending through one of the holes 24, 26, as the case may be, is aligned so as to be normal to a line 36 between the right and left anterior/superior iliac spines normal to the patient's pelvic line 38. In this regard reference is made to FIG. 3.

With the instrument thus aligned, which accomplishes the proper orientation of acetabular cup 8, the cup is inserted in the previously prepared acetabulum and impact rod 2 is impacted, whereby the cup is seated in the acetabulum. Upon the cup being so seated, coupling rod 10 and pivoting rod 14 are released whereby end 20 of rod 14 is displaced via the biasing of spring 18 to enter slot 22 for releasing the grip on the cup, whereby the instrument is removed from the cup without disturbing its seating.

It will be understood by those skilled in the art that the instrument herein described has a versatility in use in that it may be used for an acetabular cup prosthesis which is either press fitted or cemented into the acetabulum. Significantly, the instrument saves a considerable amount of operative time since it incorporates several different instruments and eliminates the time required in switching from one instrument to the other.

The instrument can be fabricated from stainless steel, chrome steel, cobalt steel or titanium so as to have a height and length and an overall weight acceptable for orthopaedic surgeons, and for meeting the demands of working within a relatively small cavity and having enough maneuvering space as is required.

The design of the instrument is such that it retains the acetabular cup in an ideal position, and holds it firmly so that even within the bony acetabulum, the cup may be maneuvered to obtain ideal alignment. The tool itself has the ability to withstand high temperatures necessary for sterilization processes prior to use. Further, its simplified design renders it easy to learn its usage and to receive wide acceptability by the orthopaedic community.

Although the invention has been described with reference to an acetabular cup having an internal rim with a particular polygonal configuration such as illustrated in the aforementioned "Howmedica" system, it will be understood that the instrument may be modified to be adaptable to any such system wherein the cup has an internal rim configuration which is circular, square, triangular, or any other shape, the same being within the scope of the invention. Thus, the instrument may be modified for use with the "Richards" system, the "Zimmer" system, the "Protek" system, the "De Puy" system, and all other systems using a press fit or cemented acetabular component.

With the above description of the invention in mind, reference is made to the claims appended hereto for a definition of the scope of the invention.

What is claimed is:

1. An instrument for orienting, inserting and impacting an acetabular cup prosthesis as part of a total hip replacement procedure, comprising:
   first, second and third rods disposed in a common plane;
   the first rod having a bottom with a shaped end and a slot in said end;
   the second rod extending angularly from the bottom of the first rod;
   the third rod displaceably coupled to the second rod and having an end receivable in the slot in the end of the first rod and shaped to match the shape thereof;

a spring captured between the second and third rods and normally biasing the third rod so that the shaped end thereof is received in the slot in the end of the first rod, whereby said first rod end is adapted for supporting an acetabular cup;

the third rod displaced against the bias of the spring, whereby the end of said third rod is displaced out of the slot to grip the acetabular cup;

a pair of holes extending through the second rod in longitudinal spaced relation, with the axis of one of said holes being in a plane angularly displaced in one direction from the common plane of the first, second and third rods and the axis of the other of said holes being in a plane angularly displaced in another direction from said common plane;

a bar extending through one of said holes in accordance with the side of a patient which is being subjected to the total hip replacement procedure;

the second rod being disposed in a plane normal to the plane in which the patient is supported and the bar being disposed normal to a line extending between the right and left anterior/superior iliac spines of the patient, whereby the gripped cup is aligned for insertion into the patient's acetabulum, and thereafter inserted therein and impacted via impaction of the first rod to seat the aligned and inserted cup; and the third rod displaced by the bias of the spring, whereby the end of the third rod enters the slot to release the grip on the seated acetabular cup, whereupon the instrument is removeable from said cup without disturbing its seating.

2. An instrument as described by claim 1, wherein:
the end of the first rod is shaped as a plurality of step-like gradations and the end of the third rod received in the end of the slot in the first rod is shaped in a plurality of matching step-like gradations, whereupon said first rod end is shaped as a plurality of continuous step-like gradations for being adapted to support one of a plurality of acetabular cups on a corresponding one of the continuous step-like gradations.

3. An instrument as described by claim 2, wherein:
the lowermost of the continuous step-like gradations is the smallest in size for supporting a smallest cup and the uppermost of said continuous gradations is the largest in size for supporting a largest cup.

4. An instrument as described by claim 2, wherein:
each of the plurality of continuous step-like gradations is polygonal in shape for engaging a polygonal shaped inner surface of the acetabular cup for supporting said cup.

5. An instrument as described by claim 3, including:
a pin extending from within the bottom of the first rod and through the lowermost of the step-like gradations at the end thereof;
the acetabular cups having an axially displaced through hole into which the pin extends when one of said cups is supported on a corresponding one of the continuous step-like gradations; and
the pin having a shoulder for limiting the extension of the pin into the cup hole.

6. An instrument as described by claim 5, wherein:
a spring is disposed within the bottom of the first rod and engages the pin in spring biasing relationship so that the pin extends a predetermined distance from the lowermost of the step-like gradations at the end of the bottom of the first rod; and
said pin is displaced against the bias of the spring disposed within the bottom of the first rod so that the uppermost of the continuous step-like gradations supports the largest acetabular cup.

7. An instrument as described by claim 1, including:
the end of the third rod being substantially parallel to the first rod;
said third rod having a first section extending from the end thereof at a first angle from the second rod; and
said third rod having a second section extending from the first section at a second angle from the second rod, said second angle being greater than the first angle.

8. An instrument as described by claim 7, wherein:
the spring captured between the second and third rods is captured between the second rod and the first portion of the third rod near the end thereof.

9. An instrument as described by claim 8, wherein:
the third rod is displaceably coupled to the second rod between the spring captured between the second rod and the first portion of the third rod and the end of the third rod below said spring.

10. An instrument as described by claim 8, wherein:
the third rod is displaced against the bias of the spring when the second section of the third rod is displaced toward the second rod by squeezing the second section of the third rod and the part of the second rod opposite said second section.

11. An instrument as described by claim 4, wherein:
the polygonal shape of the continuous step-like gradations is different than the polygonal shape of the inner surface of the acetabular cup.

12. An instrument as described by claim 8, wherein:
the pair of holes extend through the second rod in longitudinal spaced relation above the spring.

* * * * *